US009565837B2

(12) United States Patent
Bench et al.

(10) Patent No.: US 9,565,837 B2
(45) Date of Patent: Feb. 14, 2017

(54) APPARATUS AND METHOD FOR USING INFRARED THERMOGRAPHY AND BEHAVIOUR INFORMATION FOR IDENTIFICATION OF BIOLOGICALLY IMPORTANT STATES IN ANIMALS

(76) Inventors: Clover Bench, Edmonton (CA); Al Schaefer, Lacombe (CA)

(*) Notice: Subject to any disclaimer, the term of this patent is extended or adjusted under 35 U.S.C. 154(b) by 344 days.

(21) Appl. No.: 14/008,445

(22) PCT Filed: Mar. 28, 2012

(86) PCT No.: PCT/CA2012/000279
§ 371 (c)(1),
(2), (4) Date: Sep. 27, 2013

(87) PCT Pub. No.: WO2012/129657
PCT Pub. Date: Oct. 4, 2012

(65) Prior Publication Data
US 2014/0015945 A1    Jan. 16, 2014

Related U.S. Application Data

(60) Provisional application No. 61/468,492, filed on Mar. 28, 2011.

(51) Int. Cl.
*A01K 29/00*    (2006.01)
*A61B 5/00*    (2006.01)
(Continued)

(52) U.S. Cl.
CPC ............ *A01K 29/005* (2013.01); *A61B 5/002* (2013.01); *A61B 5/015* (2013.01); *A61B 5/6887* (2013.01);
(Continued)

(58) Field of Classification Search
CPC ..................... A01K 2267/0393; A01K 29/005; A01K 1/12; A01K 5/02
See application file for complete search history.

(56) References Cited

U.S. PATENT DOCUMENTS 5,442,456 A * 8/1995 Hansen ............. G06F 17/30855
386/230
7,966,971 B2 * 6/2011 Zimmerman ............ A01K 5/02
119/174
(Continued)

FOREIGN PATENT DOCUMENTS

EP            1520471 A2    4/2005

*Primary Examiner* — Obafemi Sosanya
(74) *Attorney, Agent, or Firm* — Marsh Fischmann & Breyfogle LLP; Jonathon A. Szumny

(57) ABSTRACT

The present apparatus and method provides for real-time automated, non-invasive infrared thermography information of an animal to be used for both thermal and behavioral measurement, thereby providing an earlier and more accurate predictor of onset of disease, growth states, or reproductive states in that animal. More specifically, the present system and method provide for the use of thermal images (taken, for example, at a water station) to obtain both temperature and behavioral information about one or more animals at a time, and to utilize that information to determine the health, growth, or reproductive state of the animal. The combination of thermal biometric data, such as radio frequency identification infrared thermography, and behavioral biometric information, such as behavioral fidgets can be used to detect early-onset of these biological steady and non-steady states in animals.

19 Claims, 5 Drawing Sheets

(51) Int. Cl.
*A61B 5/01* (2006.01)
*A61D 17/00* (2006.01)
*A01K 1/12* (2006.01)
*A01K 5/02* (2006.01)

(52) U.S. Cl.
CPC ......... *A61D 17/002* (2013.01); *A61B 2503/40* (2013.01)

(56) References Cited

U.S. PATENT DOCUMENTS

| | | | | |
|---|---|---|---|---|
| 2002/0108576 A1* | 8/2002 | Lely | .................... | A01K 1/12 |
| | | | | 119/14.02 |
| 2003/0004652 A1* | 1/2003 | Brunner | ................. | A01K 1/031 |
| | | | | 702/19 |
| 2004/0019269 A1* | 1/2004 | Schaefer | ................ | G01N 25/72 |
| | | | | 600/407 |
| 2006/0155172 A1* | 7/2006 | Rugg | ................... | A61B 5/1113 |
| | | | | 600/300 |

\* cited by examiner

APPARATUS AND METHOD FOR USING INFRARED THERMOGRAPHY AND BEHAVIOUR INFORMATION FOR IDENTIFICATION OF BIOLOGICALLY IMPORTANT STATES IN ANIMALS

TECHNICAL FIELD

A non-invasive apparatus and method of identifying biologically important states in animals is provided. More specifically, an apparatus and method of combining real-time, non-invasive, ethological behavioral information with infrared scanning is provided for identifying agriculturally important states, such as disease, growth, or reproductive states, in animals such as livestock.

BACKGROUND

Livestock often undergo significant exposure to transport and handling, co-mingling, auction and some time off feed and water. Collectively, these events can impede the immune system and can result in a significant incidence of disease. Such events can have considerable economic impact, for example, on the agricultural industry both with respect to health treatment costs and animal performance. Recent research has resulted in an increased understanding of the importance of animal management factors, such as transport and ante-mortem handling, in influencing both animal welfare and the food quality arising from such animals. It is known that disease and stress can have a dramatic, negative impact on animal welfare parameters and performance as well as meat quality and yield and hence the economics of the animal industries.

As would be known to a person of skill in the art, a number of diseases, such as Bovine Viral Diarrhea (BVD) type 1 and 2, Infectious Bovine Rhinotracheitis (IBR), Corona Virus, Bovine Para-Influenza (PI3) and Bovine Respiratory Syncytial Virus (BRSV), can impact livestock populations. One such disease complex, known as bovine respiratory disease (BRD), refers to a host of complex diseases, and is generally used to refer to an animal displaying an undifferentiated fever and/or other clinical signs (e.g. respiratory distress, lethargy, and loss of appetite).

The presence of BRD in intensively raised calves has caused a dependence on antibiotic treatments (including mass treatments), which, in turn, has led to a concern for the promotion of antibiotic resistant microbes. Indeed, the ability to treat BRD in cattle is becoming more difficult due to the emergence of resistant microbes (for e.g., pneumonia), or new zoontic diseases in multiple sourced, co-mingled cattle. Furthermore, recent reports have shown substantial contamination of carcass and meat products with antibiotic resistant strains of bacteria such as E. coli.

The effectiveness of treating livestock diseases, such as BRD, can depend upon the ability to detect, diagnose and treat affected animals early. The ability to achieve early detection will depend upon the information available and on the reliability of that information. For instance, when used alone, traditional clinical signs of disease provide poor diagnostic results because clinical symptoms often occur late into the course of the illness. Further, many diagnostic techniques, such as the use of acute phase proteins or hematology assessment, require the capture and invasive, in vivo collection of biological samples, which result in the significant cost of analysis and time. The requirement of the capture (and therefore restraint) of the animal in order to collect a biological sample causes stress, and the process itself is therefore introducing inaccuracies into the data collected.

Recent research has focused on alternative approaches to non-invasively determine the early identification and onset of disease in cattle. One such approach is infrared thermography, which can be used as a means of detecting the dissipation of heat in animals. Thermography operates on the principle that infrared radiation can be utilized to observe radiated heat loss and to provide an early indicator of fever because up to ~60% of the heat loss from an animal can occur in infrared ranges. The technology has been demonstrated to be effective in non-invasive identification of transport and other environmental stressors that can alter an animal's heat loss.

Another approach to non-invasive disease analysis is the commonly used "pen-checking" approach, wherein the animal caregiver observes the animal on a daily basis to detect any abnormal behavioural patterns, or clinical signs of illness (e.g. decrease in eating due to loss of appetite; see Table 1 for further examples of behavioural benchmarks). Although non-invasive, pen-checking is highly inaccurate particularly during the early stages of disease onset and leads to false-positive and false-negative results because it depends upon the skill and observations of the caregiver. Further, it is known that animals often do not display overt signs of illness (that would be detectable to a caregiver) until later in the progression of the disease, resulting in an increased risk of infection of healthy animals in a population, particularly where the animals share a source of food and water.

TABLE 1

PRIOR ART
Commonly-used clinical scores used in the bovine respiratory disease (BRD)
early disease detection

| | Clinical Score Assessment | | | | | |
|---|---|---|---|---|---|---|
| | 0 | 1 | 2 | 3 | 4 | 5 |
| Disposition, Lethargy and Behaviour | Moving around well with normal posture, Content, No signs of lethargy | Slightly depressed appearance, Holds head slightly lower than normal, Mild anorexia | Moderate lethargy and depression, Holds head low, Droopy ears, Slow to rise, Stiff | Hanging back from the rest of the herd, Recumbent or abnormal posture, Largely | Prostrate, Recumbent or abnormal posture, Not interested in surroundings, Weakness | Death |

TABLE 1-continued

PRIOR ART
Commonly-used clinical scores used in the bovine respiratory disease (BRD) early disease detection

| | Clinical Score Assessment | | | | | |
|---|---|---|---|---|---|---|
| | 0 | 1 | 2 | 3 | 4 | 5 |
| Respiratory Insult | Normal breath sounds | Very fine crackle and/or moderate cough | Fine crackle and/or moderate nasal discharge and moderate cough | movements, Anorectic depressed Medium crackle and/or moderate to severe viscous nasal discharge with cough | Course crackles and/or severe discharge with respiratory distress and obtunded lung sounds | Marked respiratory distress and/or lung consolidation |
| Digestive Insult | No insult, Normal eating and drinking | Mild or slight diarrhea with slight dehydration and reduced eating | Moderate diarrhea with 10% dehydration and reduced feed intake | Moderate to severe diarrhea with 10% or less of feed intake and more than 10% dehydration | Severe diarrhea, and less than 10% of normal feed intake | Severe diarrhea and not eating, not drinking and dehydrated |

It is also known that the identification of non-disease states in animals is important to the agricultural industry as well as to zoo and wildlife biology settings. There are many biological events in an animal's life that influence a plethora of biometric measurements and characteristics expressed. Some of these events are normal biological functions an animal will display such as when they adapt to a changing environmental temperature, a changing growth period or a changing endocrine event including puberty or estrus. Other events are less common and will include the onset of a disease state. In either disease or non-disease states the animal will be considered to be in a biologically important, non-steady state during these periods. These biologically important states may have, for example, agriculturally important consequences and implications.

Growth efficiency in animals is often defined as the gain in a particular tissue type such as muscle or milk compared to the input of resources such as feed and water. In addition to disease states, growth efficiency is an important attribute in animal agriculture as competition for limited resources increases. However, measuring growth efficiency has always been a challenge. One of the more accurate methods to monitor growth efficiency is to use indirect calorimetry which measures exactly the amount of oxygen and energy used by an animal for a given increase in gain of a specific tissue while noting that the metabolism will also give off heat (Kleiber, M. 1961. The fire of life—an introduction to animal energetics. John Wiley & Sons, Inc). Alternatively, growth efficiency can be monitored by measuring the actual feed consumed by an animal and the growth that resulted or measuring the so called gain to feed ratio (Kleiber, M. 1961. The fire of life—an introduction to animal energetics. John Wiley & Sons, Inc).

A more recent approach to monitoring growth efficiency has been to monitor the so called residual feed intake (RFI) which fundamentally is a comparison of the measured feed to gain against a known estimate for feed to gain based on scientifically accepted formulas (Basarab et al. 2003, 2007 see below). However, this later method, while reasonably accurate, requires a lengthy seventy days or more feed monitoring period which is both expensive and impractical.

It is also known that the identification of reproductive states in animals is important to biology in general and to the agricultural industry specifically. For example, reproductive states such as onset of puberty and estrus are important to identify for the purposes of reproductive efficiency, and therefore agricultural efficiency. It is known in the art that the onset of puberty and estrus are characterised by behavioural estrus which includes an increased restlessness of the animal.

There is therefore a need for non-invasive, early and accurate means of identifying biologically important states in animals. Furthermore, there is a need for a non-invasive detection means that are capable of identifying diseased animals, even in populations where there is a low prevalence of the disease.

SUMMARY

The present apparatus and method provides for real-time automated, non-invasive infrared thermography information of an animal to be used for both thermal and behavioural measurement, thereby providing an earlier and more accurate predictor of onset of disease, growth states, or reproductive states in that animal. More specifically, the present system and method provide for the use of thermal images (taken, for example, at a water station) to obtain both temperature and behavioural information about one or more animals at a time, and to utilize that information to determine the health, growth, or reproductive state of the animal. The combination of thermal biometric data, such as radio frequency identification infrared thermography, and behavioural biometric information, such as behavioural fidgets can be used to detect early-onset of these biological steady and non-steady states in animals.

Broadly speaking, an apparatus for identifying important biological states in an animal is provided, the apparatus comprising: an enclosure for receiving the animal therein;

means for animal identification mounted on the enclosure and connected to a reader for identifying when an animal is received into the enclosure; at least one infrared thermography camera mounted on the enclosure for photographing the animal to obtain infrared thermography and behavioural information from the animal; and a processor in communication with the reader and camera for receiving and processing information from the camera and the reader; wherein the information processed by the processor identifies important biological states in the animal.

Broadly speaking, a method of identifying important biological states in an animal is provided, the method comprising: providing an enclosure receiving the animal therein; receiving an animal within the enclosure; identifying the animal; photographing the animal to obtain infrared thermography images and behavioural information from the animal; processing the infrared thermography images and behavioural information; and identifying important biological states in the animal as a result of processing the infrared thermography images and behavioural information.

All documents and references referred to herein are incorporated by reference in their entirety.

FIGURES

FIG. 1 depicts an embodiment of an apparatus for combining real-time, non-invasive ethological behavioral information with infrared scanning for identifying biologically important states;

FIG. 2 shows a schematic diagram of the embodiment of FIG. 1, image as published in Schaefer et al. 2011. Research in Veterinary Science. In Press;

Figure 6:
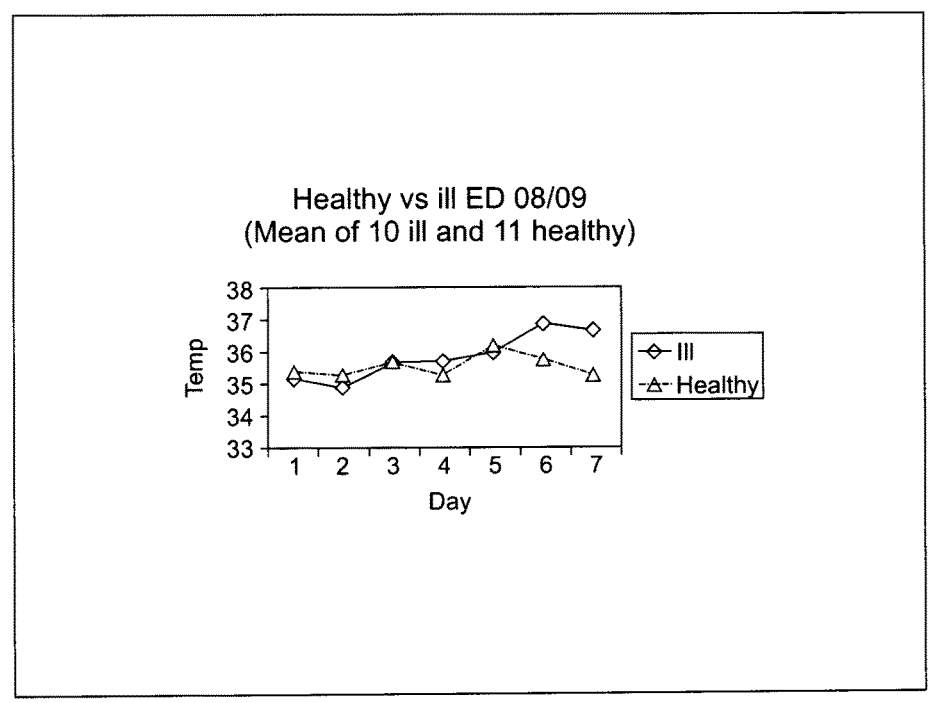
Figure 7:
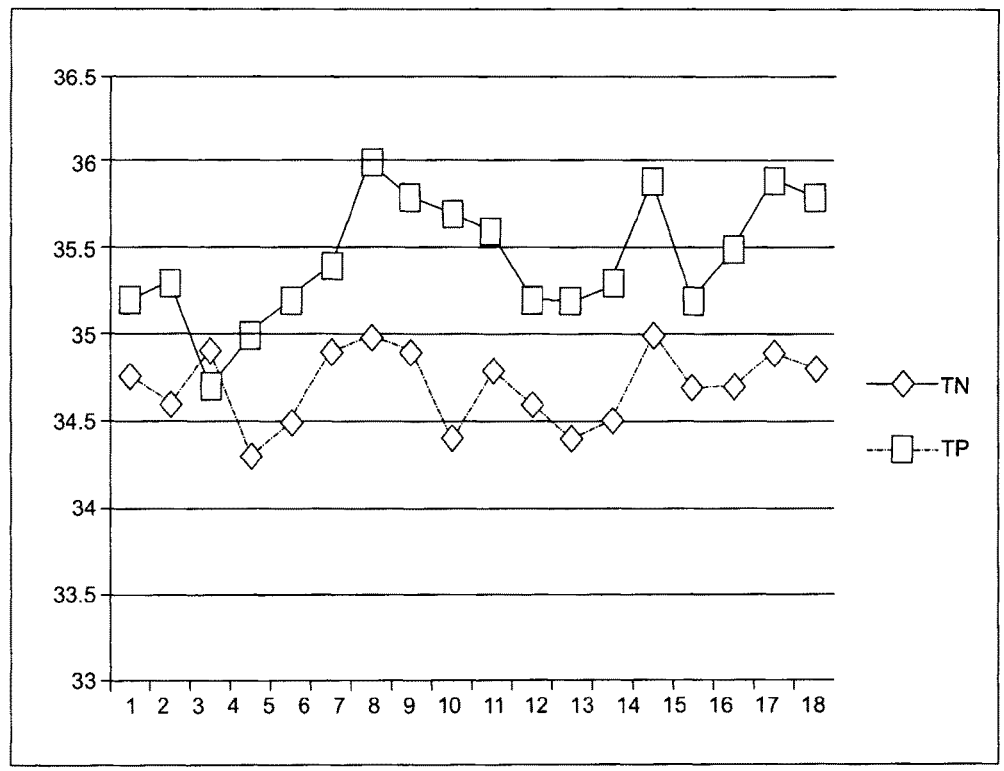

FIG. 6 shows a graphical representation of infrared thermography data plotted against time for true positive (ill) and true negative (healthy) calves with BRD; and FIG. 7 shows a graphical representation of a comparison of the infrared thermal values in a True Negative (TN) healthy animal and a True Positive (TP) ill animal for comparison. Data shows the radiated thermal value (y axis) vs the day of study (x axis).

DESCRIPTION OF EMBODIMENTS

An apparatus and method of early detection of biologically important states in animals, such as livestock, is described. In some embodiments, the biologically important states can be agriculturally important states.

More specifically, an apparatus and method of combining thermal and behavioural biometric information for the early identification of disease, growth efficiency, puberty, or estrus is provided. Infrared thermography (IRT) and ethological benchmarks may be combined to provide an early and automated identification system. While the present disclosure generally relates to beef cattle, it would be understood by one skilled in the art that the apparatus and methods provided herein may be utilized to detect disease in any animal, such as livestock species, including, but not limited to dairy cattle, pigs, and poultry.

In the present apparatus and method, automated thermal and ethological data may be collected simultaneously using at least one IRT camera and software system. Thermal data can be used in conjunction with predictive or diagnostic infrared values, alongside ethological (behavioural) predictors termed "fidgets" (i.e. the "fidget factor"), wherein both the infrared values and fidgets are both determined from the IRT thermal camera image data.

Infrared Thermography Information

Figure 1:
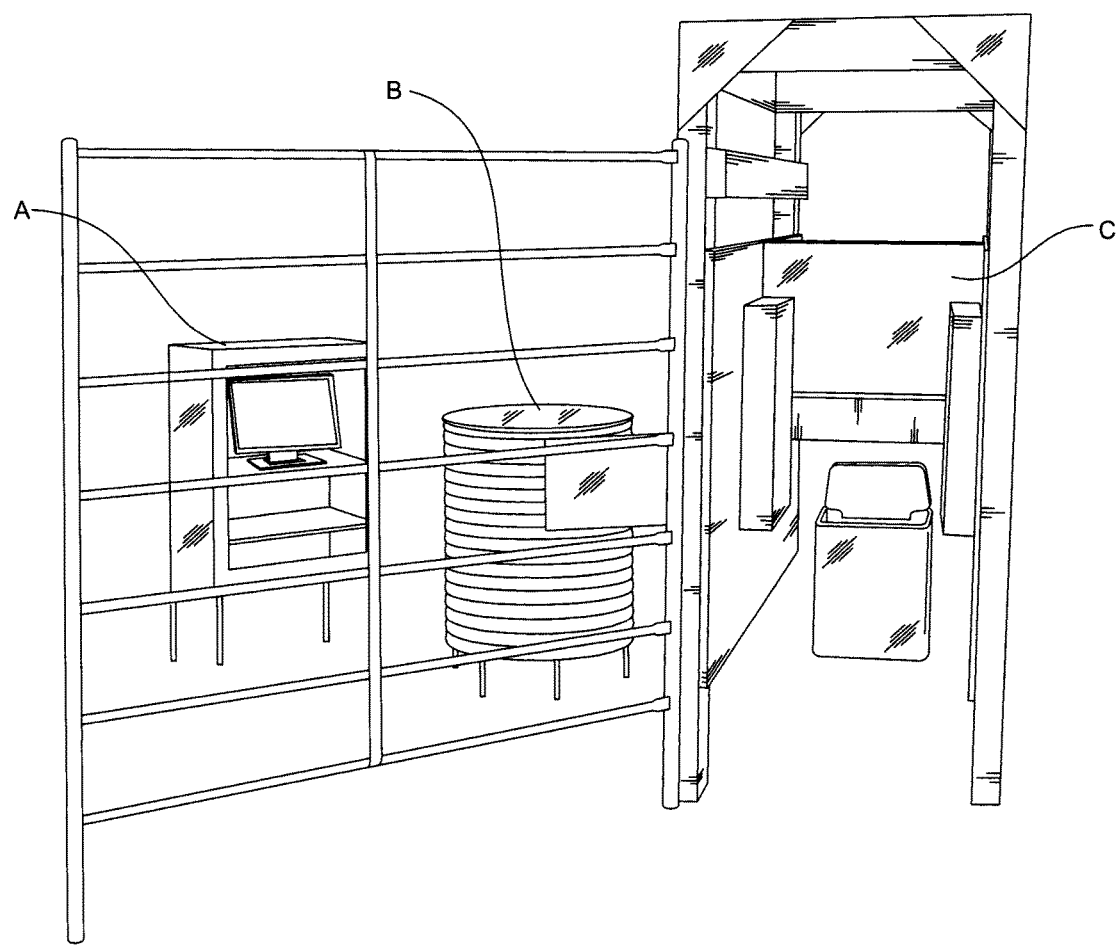

An embodiment of the present scanning apparatus is shown in FIG. 1. FIG. 1 depicts a an embodiment of an automated, radio-frequency identification-driven (RFID), multi-calf infrared scanning apparatus which can be attached to a water trough, and can comprise a data storage unit (A), camera housing (B) and a water system with an RFID antenna (C).

Figure 2:
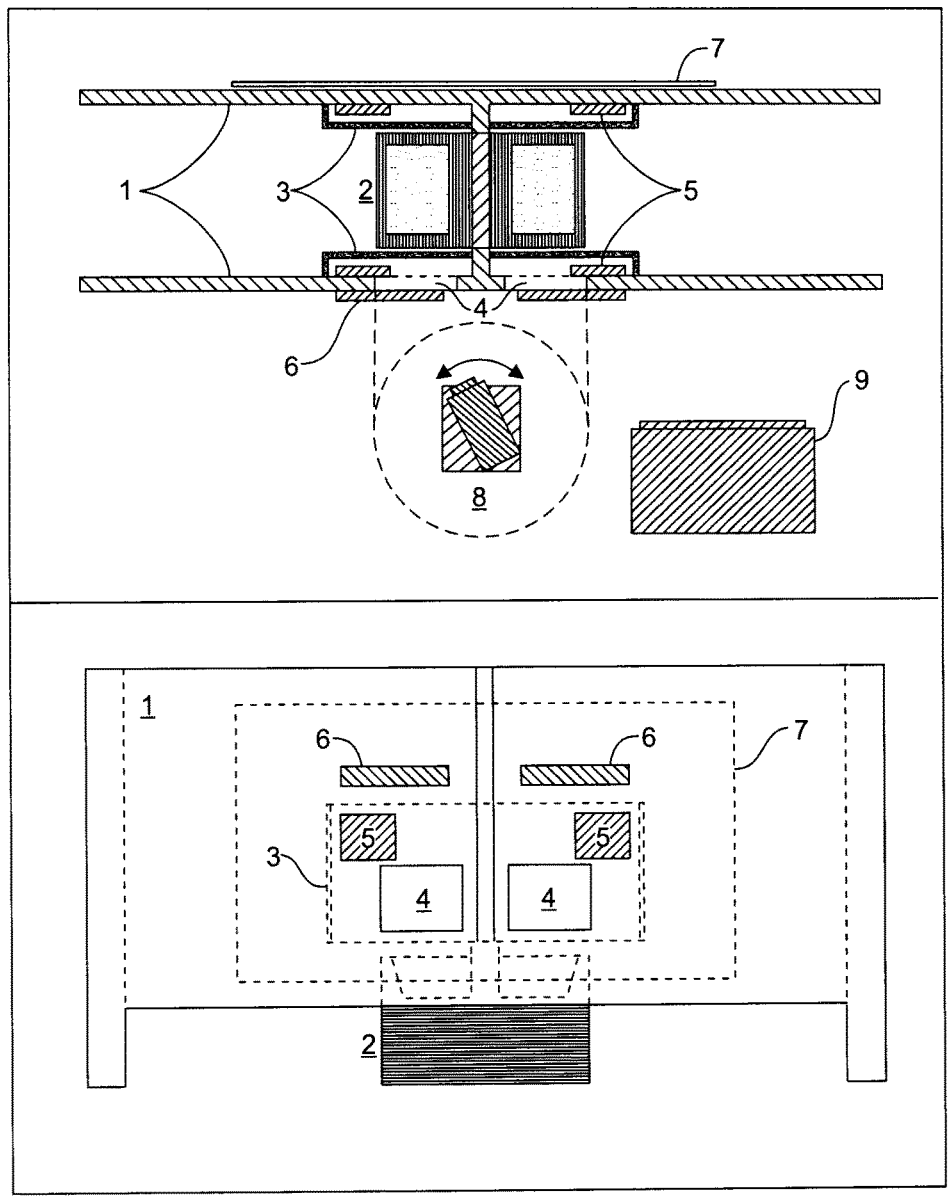
Figure 3:
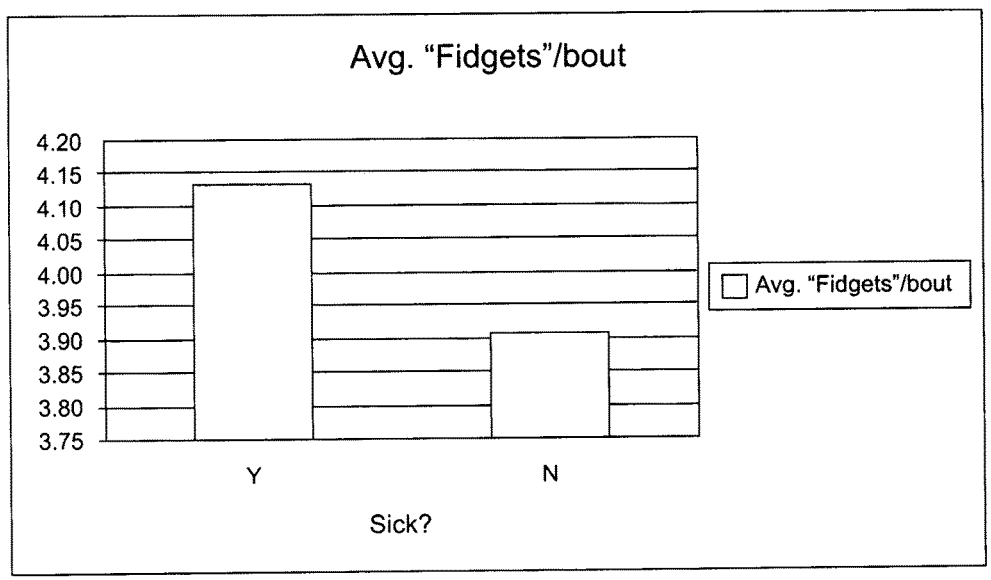
FIG. 3 shows a graphical representation of behaviour data for calves suffering from BRD, wherein the ill (sick) calves "fidget" more per drinking bout compared with healthy (not sick) calves.

Having regard to FIG. 2, the automated scanning apparatus can comprise:

An enclosure, for receiving the animal therein, wherein the enclosure can be, for example, a water or food station. In some embodiments, the enclosure can be fenced in, in other embodiments, the enclosure could simply be a pasture area. As would be understood by one skilled in the art, an enclosure can comprise any area or structure which accomplishes the functions described herein.

In the present embodiment, a water station was designed having two side panels (1), surrounding a commercially-available, two-water bowl float design (2) from Ritchie water systems (Ritchie Cattle Fountains, Conrad Iowa, USA), and optionally separated by a partition there between. The present enclosure may allow for access to the water station from two or more directions. It should be noted that a water station was utilized in the present embodiment because during illness it is known that animals cease eating, due to loss of appetite, before they cease drinking. It should also be noted that any enclosure, or other means of reducing overall movement of an animal, in a stress-free way, such that an image could be taken of the animal, could be utilized and is contemplated;

Extension panels (3) can be placed on each side of the water bowls to "centre" or frame the position animal's head, and to help keep the animal's head at the proper focal distance. A panel (1) on one side of the water bowls may be modified to facilitate a window (4) in order to view the animal while at the water station. The window may measure, for example, approximately 30 cm square;

At least two in-phase loop antennae (5), for receiving information from the animal's radio-frequency identification tags (RFID), or other such animal identification means, as applicable, may be mounted in the panels (1) adjacent to (or near) the water bowls (2), and connected to an Allfex PNL-OEM-MODLE-3 RFID control module or "reader" (6) (Allflex EID system, Allflex Canada Inc. St-Hyacinthe, P.Q.);

At least one infrared thermography camera (8). The camera (8) may, for example, be capable of obtaining at least 1-60 images/second such as a FLIR S60 broadband camera (FLIR Comp., Boston, Mass.), which may be rotably mounted adjacent to or near the windows (4). Means for electronically rotating the camera (8), such as a geared-head motor, may be connected to the camera, for powering the rotation of the camera. The camera may be used to obtain radiated temperatures around, for example, the orbital area (eye plus one centimeter surrounding the eye) of animals. The orbital eye area was chosen in the present system because it is known to provide an accurate peripheral temperature reading, thereby providing a measurement that is sensitive to both stress and disease onset. Although the thermal orbital (eye) is described herein, it is understood that any area on the animal that provides an accurate and adequate peripheral thermal reading of the animal's temperature may be used; and A control system or processor (9), for receiving and processing information from the camera (8) and the RFID antenna/reader (5, 6). For instance, the processor may be programmed to control the camera positioning, acquire the infrared image, perform the analysis of the image data, and to store the acquired information on a database. The information may be collected and received automatically upon the animal entering the enclosure, and the processor may collect the information via wireless transmission, such that information may be monitored remotely. Instrument integration, and the hardware and software used in such a thermal station was designed and developed, in part, at the Lacombe Research Centre, Lacombe, Alberta, Canada.

In one embodiment, an optional electromagnetic shielding (7) may be exposed to the holding pen on the side of the panels (1) to prevent the improper reading of RFID tags on animals that are not within the enclosure.

In operation, the present apparatus and method provide that when an animal enters the enclosure, the RFID antenna system (5, 6) can receive the identification of the animal from the RFID tags, and can signal control system (9) to rotate the camera (8), if necessary, in the direction of the animal, and to initiate capturing images of the animal's head when it becomes visible through the window (4) in the panel (1). In one embodiment, the camera/motor assembly (8), can be enclosed under a protective cover, and can be located medially between the two viewing windows (4) at a distance that provided a field of view to cover most head positions of an animal.

It is understood that mounting the infrared camera on a motor capable of rotating to at least two different scan windows (4) as signalled by the RFID reader can provide the capacity to obtain information from at least two animals at one time. For instance, the system may be designed to accommodate a second enclosure/thermography station situated parallel to the first station with the camera located centrally between the two stations, thereby at least doubling the animal handling capabilities of the system.

The present apparatus and design may enable known methods of correct thermography techniques, namely, a fixed focal length and angle with a near-still image, thereby providing accurate thermal data collection. The system can further provide non-invasive means of obtaining both thermal and behavioural (discussed below) biometric information without the need to restrict or capture the animals. It is understood that any similar system capable of providing correct thermography information, without necessitating capture and restraint of the animal, is contemplated.

Ethological (Behavioural) Information

The present apparatus and method can also provide for the use of the IRT information obtained from animals as a measurement of behavioural prediction of disease onset or other biologically important states in animals. For instance, the thermal images taken at the water station, as herein described, can be further utilized to obtain behavioural information about the animal, thereby providing means for combining the thermal (temperature) biometric information with behavioural biometric information, to provide earlier and more accurate disease detection and state identification in the animal.

Each time-stamped image taken by the automated IRT system can be classified as a behavioural "event". For example, movement of the animal at the water station can result in the camera (8) having to reset the thermal contrasts between and among the IRT pixels, thereby automatically causing a new image to be taken and time-stamped and the postural adjustment or "fidget" of the animal to be recorded. As such, depending on how much fidgeting the animal does at the water station, more or fewer images may be taken of one animal as compared to another. The images can then be used to calculate behavioural factors such as, for example, the total time the animal spent drinking, the number of drinking bouts, the length of each drinking bout, the average number of drinking bouts per day, and the number of "events" (i.e. fidgets) recorded (e.g. the number of thermal scans taken during a single drinking bout). The information can then be used, in conjunction with the thermal information to determine "true-positive" (i.e. sick) and true-negative (i.e. non-sick) disease. Accordingly, an ethological predictor of disease, referred to herein as a "Fidget Factor" can provide an additional benchmark for non-invasive disease detection and state identification.

It should be noted that different animals may fidget more or less than others in the population, and that fidgeting can further be altered due to an illness, growth state, or reproductive state. It should be known that the processor can be capable of utilizing all of the infrared thermography images of each animal (e.g. orbital (ocular), mouth, nose, ear, shoulder, and body images were all included in the behaviour data set) in order to process the fidget behaviour.

Thus, the present apparatus and method can provide for the use of infrared thermography images to be used to detect the peripheral temperature of the animal as well as the behavioural activity of the same animal, thereby providing earlier and more accurate disease detection and state identification. It is understood that the present apparatus and method can provide for two distinct sets of data or information to be generated in parallel or series. It would also be apparent that these two biometric data sets consisting of both infrared and fidget information can be used in a number of statistical assessment procedures including multiple regression and correlation, ranking and prediction indexes to enable the more accurate identification of true-positive and true negative animals.

Such detection and identification means are likely to be applicable in a variety of settings, including, for example, in bio-security and bio-surveillance circumstances.

The following examples are provided to aid the understanding of the present disclosure, the true scope of which is set forth in the claims. It is understood that modifications can be made in the system and methods set forth without departing from the spirit or scope of the same, as defined herein.

EXAMPLES

Example 1

Animals

In this example, forty (40) multiple sourced, co-mingled and transported commercial, auctioned receiver calves, which had been exposed to viral and bacterial infection for respiratory viruses including BVD, PI3, IBR, Corona and BRSV, and forty (40) retained possession calves were used. The calves were weighed, monitored for core and orbital thermal properties, blood sampled and placed onto conventional cereal grain silage with access to shelter and clean water.

Twenty (20) of these calves were obtained from the BVD and IBR antibody free herd at the Animal Diseases Research Institute at Lethbridge, Alberta, Canada. These calves were Angus×Hereford crosses and had been weaned approximately one week prior to transport to Lacombe, Alberta, Canada. The calves were an average of 550 lbs, were raised on native grass pasture and had been given a de-worming medication two weeks prior to weaning.

The calves were transported on a conventional disinfected horse trailer. On arrival at Lacombe Research Station, a transport time of approximately 5 h, the calves were co-mingled with 20 multiple sourced and commingled auctioned calves. All calves were monitored continuously for 3 weeks. All calves were observed to have continuous contact with each other by touching noses as well as sharing the same water trough, salt lick, feed bunks and bedding.

Infrared Thermography

Automatic infrared thermography images (IRT) were collected using a portable Inframetrics broadband S60 infrared scanner (FLIR® Inframetrics S60, Boston, Mass., USA). All images were taken of animals as they entered the automated infrared scanning station at the common water station located in the pen (see FIGS. 1A, B and C). In the present experiment, images specific to the orbital area of each calf were used in collecting thermal data.

All calves were thus monitored for average daily maximum temperatures (including change in temperature) and for the mean ratio values (MR). The mean ratio which was calculated as the average of daily radiated maximum temperature for a given animal divided by the average daily maximum value for the group of calves. The thermal data was verified by comparison to serology and virology blood parameters.

Ethology—"Fidgets"

Using the time stamp (which provides the hour, minute, second and date of the image obtained via a chronometer or clock), for each image taken by the automated IRT system, each image was defined as a behavioural "event" which triggered the image to be recorded. During the present example, a 4-minute interval between drinking events (known as the bout criterion interval; BCI) was used to determine the termination or conclusion of one drinking bout and the start of another. Accordingly, the same infrared images were used in the analysis of both thermal and ethological data sets, albeit, the ethological data set included "all images", while the thermography data set included "orbital images" only.

Results

In the forty (40) multiple-sourced and co-mingled commercial calves, there were 10 animals out of the 40 identified as "ill" (true-positive animals). This identification was made by virtue of displaying clinical scores of 3 or higher (see Table 2), and by orbital infrared values of 35.1° C. compared to healthy animals (or true negative animals) having a temperature of 34.8° C. Clinical illness was verified by statistically significant haematology values. In addition, the ill calves demonstrated an approximately 40% increase in the blood cortisol values (deviating from an average of 52 nmol/L in healthy calves to over 70 nmol/L in ill calves). Results demonstrate that haematology data for the forty (40) control retained possession calves displayed normal haematology values.

It is known that four to six days prior to the display of clinical signs and lab verification of illness, infrared orbital scans can be 71% efficient (combined true positive and true negative values) at early identifying ill animals compared to either clinical scores alone (55% efficiency) or rectal temperatures alone (59% efficiency). This is supported in the present example where the non-invasive collection of orbital infrared temperatures, alone, was 73% efficient at identifying ill animals 2-7 days before clinical symptoms detectable by "pen-checking".

Figure 4:
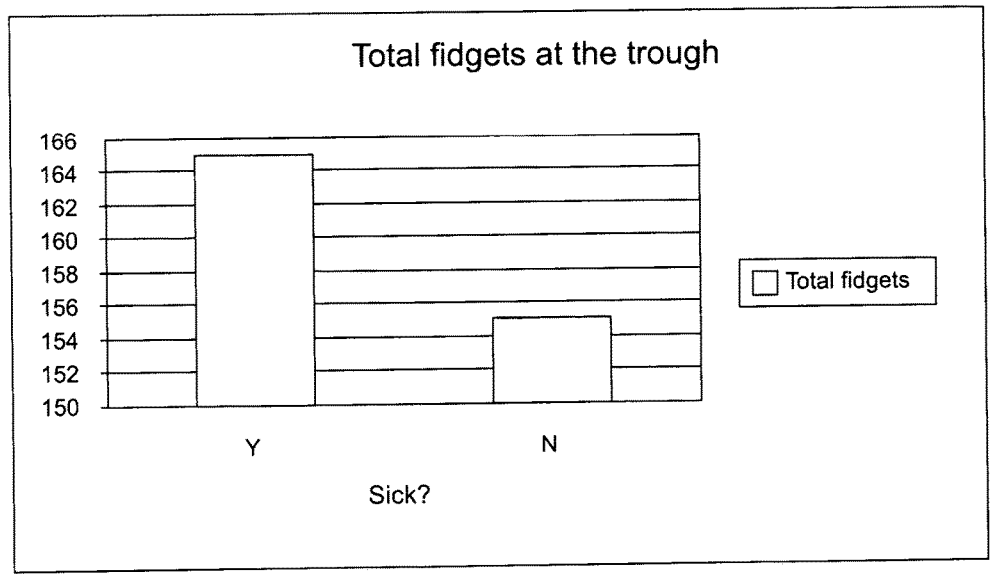
FIG. 4 shows a graphical representation of behaviour data for calves suffering from BRD, wherein the ill (sick) calves "fidget" more overall than healthy (not sick) calves.
Figure 5:
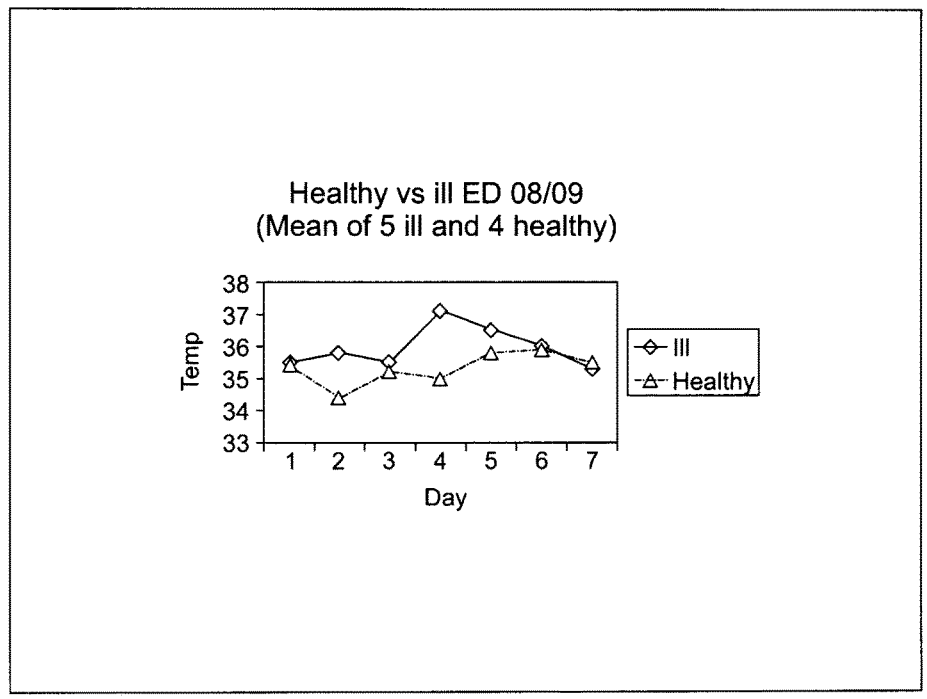
FIG. 5 shows a graphical representation of infrared thermography data vs time of true positive (ill) and true negative (healthy) calves with BRD.

Further analysis of all thermal images recorded through the automated IRT system, and based on a 4 minute drinking bout interval, results show that true-positive or "sick" animals have a tendency to "fidget" more than "non-sick", true-negative animals (FIGS. 4 and 5). Sick (true-positive) animals were found to have a greater number of IRT images taken during each drinking bout. This is despite overall drinking behaviour, which includes the drinking duration and the number of drinking bouts, being the same in sick and healthy (true-negative) animals. Based on the number of average fidgets (events) per bout in sick and healthy animals, a behavioural predictor or "Fidget Factor" of 4 fidgets per drinking bout was determined to be a possible indicator of disease.

False-negative and false-positive animals were not included in this data set, as analysis focused on true-sick and true-healthy animals only.

TABLE 2

Means ± SD of haematology values for the forty multiple sourced co-mingled calves. White blood cells (WBC) and all other differential cells = cells × $10^9$, Red blood cells (RBC) = cells × $10^{12}$, hgb = g/L

|  | WBC | Neut | Lymph | Mono | Eosyn | Baso | RBC | HgB | Hct % | N/L |
|---|---|---|---|---|---|---|---|---|---|---|
| Healthy | 9.12 | 1.22 | 5.56 | 0.98 | 1.28 | 0.07 | 8.83 | 11.98 | 35.4 | 0.24 |
| SD (n = 30) | 1.65 | 0.83 | 1.15 | 0.51 | 0.87 | 0.07 | 0.94 | 1.08 | 3.8 | 0.22 |
| Ill (BRD) | 12.39 | 3.33 | 5.24 | 2.11 | 2.14 | 0.13 | 7.94 | 11.24 | 34.4 | 0.82* |
| SD (n = 10) | 3.78 | 3.23 | 2.26 | 1.62 | 1.67 | 0.01 | 1.04 | 0.91 | 3.6 | 0.91 |
| P value | 0.01 | 0.01 | 0.55 | 0.01 | 0.01 | 0.02 | 0.01 | 0.04 | 0.41 | 0.01 |

Statistical separation based on least squares analysis (two tailed t-test).
*N/L ratio for ill animals was either very high or very low.

Haematology, Endocrine and Serology Data

With respect to laboratory analysis, salivary and serum cortisol was analysed using a known enzymatic assay from collected samples. Hematology analysis and differential counts were conducted on a Cell-Dyne model 3700 hematology analyser (Abbott Labs™, Mississauga, Ontario). Serology assessment was conducted by Prairie Diagnostic Services™ (Saskatoon Saskatchewan) and assessment was carried out for the BRD viruses, Bovine Viral Diarrhea (BVD) type 1 and 2, as well as Infectious Bovine Rhinotracheitis (IBR) via serum neutralization tests.

Additional assessment for Corona virus, Bovine Parainfluenza (PI3) and Bovine Respiratory Syncytial Virus (BRSV) were conducted by ELISA using methods known to one skilled in the art. Antibody concentrations (units) for BVD, IBR, BRSV, PI3 and Corona were obtained as follows:

((mean net optical density of sample−mean net optical density of fetal bovine serum)/(mean net optical density of positive standard−mean net optical density of fetal bovine serum))×100

The ranking of antibody titre scores was as follows: for BVD and IBR 0-2=negative, 3-13:1=suspicious, 14-40:1=low, 41-80:1=moderate, >80:1=high. For BRSV, PI3 and Corona <10=negative, 11-13=suspicious, 14-50=low, 51=100=moderate, >100=high.

Example 2

Animals

In this example, further trials were conducted on 100 multiple sourced, co-mingled, transported and weaned commercial calves. These calves were procured from two primary sources with 17 from the ADRI herd at Lethbridge, Alberta, Canada and 83 procured from commercial auction facilities. These calves were themselves purchased through auction from two separate locations. The calves were brought to the Lacombe Research Centre (LRC) Beef Research unit, weighed, blood sampled, core temperatures recorded and then placed into clean receiver pens with wood shavings bedding and free access to water and cereal grain silage.

Methods

Continuous, automatic infrared and behavioural data was captured on all animals for a three-week period (except when power supply or solar loading glitches caused a failure in the system), as described in Example 1.

Results

In the present example, thirty seven animals were identified as "at risk" of BRD by the "pen checking" technique. Of these animals, 24 were subsequently verified by objective lab data as being true positive (TP) and 13 were identified as false positive. Hence, the incidence of false negatives and positives is again comparatively high when pen checking clinical scores alone are used to identify BRD.

In the calves identified as true positive for BRD, the IRT temperatures were on average 36.7° C. compared to the true negative animals at the same time at 35.6° C. (P<0.05). FIGS. 6 and 7 demonstrate the relationship between true-positive and true-negative animals for calves with the most complete clinical score and infrared data, and show that the infrared scores detected animals that were verified to display BRD several days before the clinical "pen checking" scores.

Using the "Fidget Factor" predictor generated and defined in Example 1 to detect sick animals (an average of 4 fidgets per drinking bout over a 24 hour period), no significant differences were found in the present Example 2. Some possible explanations may include either the need to alter the drinking bout interval or due to the high rate of false negatives in calf group. The present example also experienced higher than usual electrical glitches, which may have made the ethological data set less robust. Current research on adjusting the BCI and the fidget predictor value is required and continues.

Example 3

Animals

In the present Example 3, investigations were carried out on a total of sixty-five (65) receiver calves. These calves consisted of 54 retained possession, low disease incidence animals from the Lacombe Research Centre (LRC) Beef Research fall calving herd and a further eleven (11) calves from the high-health, closed herd located at the Animal Disease Research Institute (ADRI) at Lethbridge, Alberta, Canada. The ADRI calves were unique in that they displayed no antibodies to either BVD or IBR virus and therefore would be susceptible to BRD-causing viruses. Calves from both herds were commercial crossbred cattle of British× Continental breed. All calves had been weaned and transported to the LRC beef unit prior to the study. The animals averaged 220 kg at the start of the study.

Methods

To simulate typical marketing conditions all calves were co-mingled and transported to a local auction facility within one hour of the LRC beef unit. The calves were then offloaded and kept in pens overnight without feed or water. The cattle were loaded onto a commercial carrier and returned to Lacombe, Alberta, Canada the following day for processing.

On arrival at the LRC beef unit the calves were weighed, blood sampled, core temperature recorded, clinically scored and then placed into receiver pens containing straw bedding and with free access to water and a cereal grain silage. The calves were subsequently "pen checked" daily for signs of illness and IRT values were recorded continuously using the present system and method as defined herein. Behavioural "events" and/or fidgets were monitored and an alternative "Fidget Factor" for disease was determined based on various intervals between drinking bouts (e.g. 3 or 5 minutes, rather than 4 minutes utilized in Example 1). In addition, preliminary live observations were conducted to determine which specific facial movements prompted IRT images to be recorded as events (i.e. to define the specific mechanics of a "fidget"). It is contemplated that such observations could be further enhanced by classifying and defining the actual fidget behaviour by, for example, video analysis.

Hematology values for all animals were assessed on a CellDyn™ hematology analyser. Clinical scores were assessed using a point system (see FIG. 2) and core or rectal temperatures were recorded using a chute side digital temperature probe.

Results

Based on the pen checking information, two of the sixty-five calves were considered to be at risk of BRD. Taken together with data available at the time of processing (core temperatures of 40° C. or higher) four of the sixty-five animals would have been diagnosed as true positive for BRD. However, two of these animals were subsequently determined to be false positive by hematology analysis (white blood cell numbers and neutrophile/lymphocyte ratios), core temperature and clinical score. The use of the same analysis would also have classed eleven (11) of the calves as true positive (TP) and 20 as true negative (TN) with the remaining 34 as intermediate health. Three of the true positive (TP) animals were from the ADRI BVD and IBR antibody free herd and 8 from the LRC herd. The average values for these animals both at the start and end of the assessment period are shown in Table 3.

TABLE 3

Average Health Values ± SD for the Example 3 calves

|  | Core Temp C. | Clinical Score | WBC × 1000/μl | N/L ratios |
|---|---|---|---|---|
| March 13 ave | 102.8 | 3.18 | 12 | 0.273 |
| SD | 0.65 | 1.15 | 2 | 0.19 |
| April 1 ave | 102.6 | 2.95 | 9 | 0.129 |
| SD | 0.98 | 1.75 | 2 | 0.101 |

Infrared Values

In excess of 20,000 thermal data points were collected on the 65 calves over the two week assessment period using the automated thermal station located at the cattle water system. The average radiated temperature value for all calves during this period was typically between 33-35° C. The overall radiated thermal value for the true-negative calves for the entire observation period was 34.7° C.±0.57° C. and the value for true-positive calves 35.4° C.±0.58° C. (see FIG. 9).

Live behavioural observations were also performed in this Example 3 to increase the understanding of why true-positive calves generated greater numbers of IRT images (when all images were included) compared with true-negative calves. These observations suggest that shifts in posture or stance, eye blinks, leg movements, tongue flicks, and ear twitches may cause the IRT pixels to recalculate contrasts, thereby determining it is time to take a new image.

With respect to the data per se, the calves used in the present study were comparatively low stress and expressed a low incidence of BRD of approximately 17%. Of interest however, was the observation that conventional industry standard practice of using pen checking as the primary tool for identifying BRD would have identified only two animals and even with the addition of core temperature data at the time of processing only four animals were identified as at risk of BRD and of those, two were subsequently identified as being false positive identifications. In other words, once again, one of the primary challenges with conventional pen checking or clinical score methods for detecting BRD is with the incidence of false negatives.

Example 4

Cortisol Data

Salivary and serum cortisol analysis were performed for all animals in the foregoing Examples 1-3 (see Table 4). An ELISA assay system, developed at Lacombe Research Centre, was utilized.

In all three Example data sets the cattle were identified as true positive (TP) for bovine respiratory disease (BRD) or true negative (TN) using the hematology, core temperature and clinical score criteria identified in each of the foregoing method sections. Least squares analysis (t-tests) for the cortisol data has also been performed.

Cortisol assays were conducted on blood and saliva samples collected when the cattle arrived at the Lacombe Beef Research Centre and when an animal was identified as suspect for BRD. Cortisol data displayed considerable variation both within and between the studies performed in Examples 1-3. Some of this variation is likely due to variation in animal populations, procurement procedures and animal history among the groups. There is also likely to be some variation in stress susceptibility across cattle groups from experiment to experiment.

Table 4 represents overall averages for the animals, without correction for the present data set for animals displaying health aberrations for non-BRD reasons such as transport stress, mechanical insults such as lameness or other metabolic reasons such as dehydration. There were a few of these animals identified and they could arguably cause some bias in the data set. Nonetheless, cattle identified as TP for BRD also show a trend towards or an actual statistical increase in cortisol values. Some animals observed also tended to fall into an intermediate group for BRD identification. Again, as described in the methods section, a true negative animal would have displayed a score value of 0 or 1 for temperature values>40° C., WBC counts of >10 or <7×10$^3$/μL, an N/L ratio of <0.1 or >0.8 and a clinical score of <3. A true positive animal would display a value of 3 or 4 of these criteria and the intermediate animals would display a value of 2. As with the other laboratory criteria, these intermediate animals also tended to display an intermediate cortisol value (data not shown).

TABLE 4

Salivary and serum cortisol values in weaned and receiver calves identified as true positive (TP) or true negative (TN) for BRD

| Data Year | Salivary Cortisol nmol/L Mean | Std. Dev. | P Value Salivary Cortisol | Serum Cortisol nmol/L Mean | Std. Dev | P value Serum Cortisol |
|---|---|---|---|---|---|---|
| 2007 TP | 3.16 | 3.0 | NSD | 70.96 | 19.7 | P = 0.1 1T-test 2tail, 0.05 |
| 2007 TN | 2.95 | 3.2 |  | 52.4 | 34.9 |  |
| 2008 TP | 5.82 | 2.86 | P = 0.01 | 139.7 | 87.8 | P = 0.1 1T, 0.5 2T |
| 2008 TN | 3.92 | 1.27 |  | 113.3 | 31.1 |  |
| 2009 TP | 2.97 | 2.47 | P = 0.06 | 123.6 | 61.2 | P = 0.1 1T, 05. 2T |
| 2009 TN | 2.05 | 1.26 |  | 103.3 | 36.1 |  |

These results demonstrate that animals displaying BRD demonstrated a higher infrared radiated temperature and a higher degree of variation associated with that temperature. The cortisol data is also consistent with this finding showing that BRD animals generally display a higher cortisol value with greater variation.

Example 5

Fidget Value and Growth Efficiency

As an alternative to the methods discussed in the Background section above, evidence has been reported that demonstrates the use of infrared thermography to classify animals into more efficient and less efficient growth categories (Schaefer, A. L., Basarab, J., Scott, S., Colyn, J., McCartney, D., McKinnon, J., Okine, E. and Tong, A. K. W. 2005. The relationship between infrared thermography and residual feed intake in cows. J Anim Sci 83(Suppl. 1):263). It is known that animals that are more efficient at growth can display a lower heat loss to the environment. However, the components that make up or account for this difference in efficiency and energy loss are less apparent. To this end, the present apparatus and methods can be used to show that animal behaviour or so called "fidgeting" can be partially responsible for this differential energy use. As such, measuring these "fidgets" would have utility in differentiating animals with different growth efficiency. This Example 5 is provided as a non-limiting example of implementing this principle.

Eight crossbred mature cows were used in the present example to test whether a fidget measurement also ranked with both a measure of growth efficiency (Residual Feed Intake, RFI) and a measure of energy loss (infrared thermography). The cattle were fed a balanced alfalfa cube based diet which met 1.25 times the maintenance nutritional requirement for these animals. The cows were housed in outdoor pens with free access to fresh water and a straw bedded area.

The relative growth efficiency for these animals, referred to as the residual feed intake, had been previously determined using a feed bunk monitoring system to record exact feed consumption and weight gain as described by Basarab et al (Basarab, J. A., McCartney, D., Okine, E. K. and Baron, V. S. 2007. Relationships between progeny residual feed intake and dam productivity traits. Canadian Journal of Animal Science 87(4):489-502: Basarab, J. A., Price, M. A., Aalhus, J. L., Okine, E. K., Snelling, W. M. and Lyle, K. L. 2003. Residual feed intake and body composition in young growing cattle. Canadian Journal of Animal Science 83(2): 189-204).

For infrared and fidget measurements the cows were monitored postprandial between a 24 h feed period. In other words the animals were off feed during the time of monitoring. However, all animals had free access to a water station and when the cows attended the water station they triggered an infrared scanning system which included a radio frequency identification tag (RFID) thereby recording both their station attendance frequency and their facial infrared characteristics.

The daily average values for the infrared scans for the half of the animals with the lowest efficiency and the half of the animals with the highest value are summarized and shown in Table 5 along with the known RFI feed efficiency values for the cow group of 8 animals. The RFI values basically report what an individual animal's actual feed intake was (as measured by the bunk monitoring systems) compared to what would be a predicted feed intake for that animal based on her body weight and growth. For example, as explained by Basarab et at (2003, 2007) an animal with an RFI value of −1 represents a cow that consumed 1 kg per day less feed than what would be expected and an RFI value of +1 represents an animal that consumed 1 kg of feed more than what would be predicted. Lower RFI values can represent more efficient cows. In addition as shown in Table 5, the fidget values or number of thermal station triggering events were also collected. This data is expressed as the total number of fidgets per animal per day within four minute drinking bouts.

Using conventional ranking statistics (Spearman Ranking: Tuckman. 1978. Conducting Educational Research, Second Ed. Harcourt Brace Jovanovich Inc. New York) the animals in the present study displayed a significant (P<0.05) rank order of thermal values against known RFI values. The animals with the lowest thermal values also displayed the lowest RFI values and the lowest number of fidget events.

This example demonstrates that a fidget value can have utility in identifying animals displaying different production (growth) efficiency.

TABLE 5

Comparative values for RFI and IRT in two groups of mature cows

| Category | Mean RFI Value | Mean IRT Value ° C. | Mean Fidget Value Total/ day/4 min drinking bout | Spearman rank value of fidget with RFI |
|---|---|---|---|---|
| Higher efficiency (low RFI) four cows | −1.3 | 10.6 | 4 | P < 0.05 |
| Lower efficiency (high RFI) four Cows | 0.41 | 13.2 | 9 | |

Example 6

Fidget Value and Estrus

It is known in the art that there is a link between restless behaviour and estrus in animals.

Behavioural estrus indicators are the primary means in which producers determine whether dairy cows are in estrus (ie have ovulated or are ready to ovulate). Behavioural indicators of estrus include increased activity such as mounting events, pacing/walking, as well as general restless behaviour (eg. lying down and standing up, walking, stepping, and shifting, but also includes many other more subtle behaviours; Pollock, W. E. and Hurnick, L. F. 1979. Effect of two confinement systems on estrus 436 detection and diestrus behaviour in dairy cows. Can. J. Anim. Sci. 59: 799-803; Walton, J. S, and King, G. J. 1986. Indicators of estrus in Holstein cows housed in 468 tie stalls. J. Dairy Sci. 69: 2966-2973).

Cows housed in free-stalls exhibit 4 times more activity and restless behaviour during estrus (Kiddy, C. A. 1977. Variation in physical activity as an indication of estrus in dairy 414 cows. J. Dairy Sci. 60: 235-243). Cows housed in tie-stalls exhibit 2.75 times more activity and restless behaviour during estrus (when compared with cows not in behavioural estrus). Similar findings have been reported when pedometers were used to measure activity and restless behaviour during estrus in free-stalls (Roelofs, J. B., van Eerdenburg, F. J. C. M., Soede, N. M. and Kemp, B. 2005. 451 Pedometer readings for estrous detection and as predictor for time of ovulation in dairy 452 cattle. Theriogenology. 64: 1690-1703; Roelofs, J., López-Gatius, F., Hunter, R. H. F., van Eerdenburg, F. J. C. M. and 447 Hanzen, C. 2010. When is a cow in estrus? Clinical and practical aspects. 448 Theriogenology. 74: 327-344). While pedometers on cows continuously tie stalled have been unable to detect behavioural estrus based upon walking activity measures alone (Felton, C. A., Colazo, M. G., Ponce-Barajas, P., Bench, C. J., and Ambrose, D. J. 2012. Dairy cows continuously-housed in tie-stalls failed to manifest activity changes during estrus. Can. J. Anim. Sci. (in press)), the use of a more subtle behavioural biometric of restless behaviour has the ability to capture behavioural estrus even in confined cows.

Because the fidget biometric, as described within the present specification, can be an accurate and reliable measure of restless behaviour when an animal is standing in a confined space, the use of this type of fidget measure also has the means of capturing restless behaviour exhibited during estrus. As such, the apparatus and methods described herein can identify reproductive states such as estrus.

Example 7

Further Fidget Data (ED08/09 Sample)

Included are calculations on a calf bovine respiratory disease (BRD) data set referred to as ED08/09 (calves analysed in 2008 and 2009).

Briefly, a true positive (TP) animal was one that displayed 3 or 4 out of 4 for a high white blood cell count, a high neutrophile/lymphocyte ratio, an elevated clinical score and an elevated core (rectal) temperature. These criteria are defined in publications known in the art. By contrast, a true negative (TN) animal was one that displayed a score of either 0 or 1 out of 4.

Of the ED08/09 data set for 21 animals, 11 of the calves met a TP criteria and 10 met a TN criteria. In other words the prevalence of BRD in this data set was 52%. This result is very similar to the multiple sourced, commingled transported and weaned calves studied eleswhere and is typical for calves of this type in general.

The biometric data collected from the ED08/09 animals for predicting early disease onset included the absolute infrared value for the eye maximum determination, the mean ratio of the individual calf eye maximum value compared to the group mean maximum value, the so called MR value, and thirdly, the fidget value for those animals calculated from the same infrared image data set. The five minute fidgets/bout/calf/day information was used. The data used was for the day the animals were verified as TP or TN (so-called pull day) and the four days prior to that time.

One approach to determine the relative contribution a given data set has to an overall prediction or ranking of variables is to use a multiple regression approach and also a discriminant analysis (sometimes called stepwise regression) or logistic regression analysis. Different statistical programs will use different names, for example SAS uses discriminant analysis and MedCalc™ uses the term logistic regression.

Using the ED08/09 data, the value for correct TP vs. TN identification using a single biometric measurement was between 57-68%. However, combining all three biometric measurements raised the overall correct identification of animals into disease class (both TP and TN) to 83.5%. This improvement in correct classification is significant and also offers the ability to identify BRD before the pull day unlike prior art methods.

One method for ranking the relative importance of each biometric measurement in a multi-regression model is to obtain the r value (correlation value), square this value and multiply by 100 to obtain the relative percentage importance of a biometric measure or the proportion of the variance that a particular biometric value can account for. For example, with a situation like calving difficulty in heifers (dystocia) it has been determined that the relative ranking of the importance of factors would be as follows; birth weight and pelvic width of the heifer=30%, heifer age 10%, calf birth weight=7% and so on. With the BRD model above the highest ranking (value for predicting BRD onset) for all days was for the orbital absolute infrared value at 33%, next was the fidget value at 16% and the MR value at 10%.

The scope of the claims should not be limited by the preferred embodiments set forth in the examples, but should be given the broadest interpretation consistent with the description as a whole.

We claim:

1. An apparatus for identifying important biological states in an animal in real-time, the apparatus comprising:
   an enclosure for receiving the animal therein;
   animal identification means mounted on the enclosure and connected to a reader for identifying when the animal is received into the enclosure;
   at least one infrared thermography camera mounted on the enclosure for photographing images of the animal, the images simultaneously obtaining both infrared thermography information and fidget information about the animal, the photographing of the images being triggered by the animal's fidgeting behaviour; and
   a processor for receiving and processing the animal identification information, the infrared thermography information and the fidget information to determine the biological state of the animal, the biological states being selected from the group consisting of a disease state, a non-steady state growth period, the onset of puberty, and the onset of estrus.

2. The apparatus as claimed in claim 1, wherein the apparatus is automated.

3. The apparatus as claimed in claim 1, wherein the enclosure further comprises a water station or food station to be accessed by the animal.

4. The apparatus as claimed in claim 3, wherein the enclosure is configured to allow access to the water or food station from one or more directions.

5. The apparatus as claimed in claim 1, wherein the enclosure further comprises panels for positioning the animal's head in front of the camera and to assist in keeping the animal's head at a proper focal distance from the camera.

6. The apparatus as claimed in claim 1, wherein the animal identification means comprises at least two in-phase loop antennae for receiving information from a radio-frequency identification tag (RFID) on the animal.

7. The apparatus as claimed in claim 1, wherein the camera is capable of obtaining images at a rate of at least 1-60 images/second.

8. The apparatus as claimed in claim 1, wherein the camera is rotably mounted to the enclosure.

9. The apparatus as claimed in claim 1, wherein the processor is in wireless communication with the reader and camera for wirelessly receiving the animal identification information, the infrared thermography information and the fidget information.

10. The apparatus as claimed in claim 1, wherein the processor can remotely monitor the reader and camera.

11. A method of identifying important biological states in an animal in real-time, the method comprising:
    providing an enclosure for receiving the animal therein;
    receiving an animal within the enclosure;
    identifying the animal;
    photographing images of the animal with an infrared thermography camera, the images simultaneously obtaining infrared thermography information and fidget information about the animal, the photographing of the images being triggered by the animal's fidgeting behaviour; and
    processing the animal identification information, the infrared thermography information and the fidget information to identify the biological state of the identified animal, wherein the biological state is a predictor of onset of disease, growth states, and reproductive states in the animal.

12. The method as claimed in claim 11, wherein the method is automated.

13. The method as claimed in claim 11, wherein the method further comprises signaling a control system for rotating the camera in the direction of the animal.

14. The method as claimed in claim 11, wherein the method further comprises obtaining radiated temperatures around the orbital area of the animal.

15. The method as claimed in claim 11, wherein identifying the animal is accomplished by an RFID antenna system mounted on the enclosure to receive the identification from an RFID tag on the animal.

16. The method as claimed in claim 11, the method further comprising using both infrared and fidget information in statistical assessment procedures to identify the biological states in the animal.

17. The method as claimed in claim 16, wherein the biological state is selected from the group consisting of a disease state, a non-steady state growth period, the onset of puberty, and the onset of estrus.

18. The method as claimed in claim 11, the method further comprising obtaining the infrared thermography information and fidget information postprandial.

19. The method as claimed in claim 18, wherein the postprandial period is between a 24 hour feed period.

* * * * *